US008957962B2

United States Patent
Arai et al.

(10) Patent No.: US 8,957,962 B2
(45) Date of Patent: Feb. 17, 2015

(54) DEFECT CORRECTING METHOD AND DEFECT CORRECTING DEVICE FOR AN ELECTRONIC CIRCUIT PATTERN

(75) Inventors: Takeshi Arai, Yokohama (JP); Nobuaki Nakasu, Kawasaki (JP)

(73) Assignees: Japan Display Inc., Tokyo (JP); Panasonic Liquid Crystal Display Co., Ltd., Himeji-shi (JP)

( * ) Notice: Subject to any disclaimer, the term of this patent is extended or adjusted under 35 U.S.C. 154(b) by 886 days.

(21) Appl. No.: 12/784,936

(22) Filed: May 21, 2010

(65) Prior Publication Data

US 2010/0302360 A1 Dec. 2, 2010

(30) Foreign Application Priority Data

May 27, 2009 (JP) ................................. 2009-127619

(51) Int. Cl.
*H04N 7/18* (2006.01)
*H01L 21/66* (2006.01)
*G01N 21/95* (2006.01)
*G01R 31/309* (2006.01)
*G01N 21/956* (2006.01)

(52) U.S. Cl.
CPC ............ *H01L 22/20* (2013.01); *G01N 21/9501* (2013.01); *G01R 31/309* (2013.01); *G01N 21/956* (2013.01); *G01N 2021/9513* (2013.01); *H01L 22/12* (2013.01)
USPC .......................................... 348/126; 349/192

(58) Field of Classification Search
CPC ............... G01R 31/309; G01N 21/956; G01N 21/9501; G02F 1/136268; G02F 1/136254
USPC ........................ 348/126; 438/14–18; 349/192
See application file for complete search history.

(56) References Cited

U.S. PATENT DOCUMENTS

| 4,305,097 | A | * | 12/1981 | Doemens et al. | ............. 348/126 |
| 5,162,742 | A | * | 11/1992 | Atkins et al. | .................... 324/523 |
| 5,171,709 | A | * | 12/1992 | Donelon et al. | ................ 427/595 |
| 5,309,108 | A | * | 5/1994 | Maeda et al. | ................ 324/501 |
| 6,091,846 | A | * | 7/2000 | Lin et al. | ....................... 382/145 |
| 6,900,092 | B2 | * | 5/2005 | Ajmera et al. | ................ 438/231 |
| 7,274,813 | B2 | * | 9/2007 | Maeda et al. | ................ 382/141 |

(Continued)

FOREIGN PATENT DOCUMENTS

| JP | 09-307217 | 11/1997 |
| JP | 2004-279244 | 10/2004 |

(Continued)

*Primary Examiner* — Jeremaiah C Hallenbeck-Huber
(74) *Attorney, Agent, or Firm* — Antonelli, Terry, Stout & Kraus, LLP.

(57) ABSTRACT

Provided is a defect correcting device for an electronic circuit pattern, which is capable of making a defect seed obvious, and normalizing a pixel or forming a pixel into a semi-black spot. A defect correcting device for an electronic circuit pattern includes: an imaging unit for irradiating a defective portion of the electronic circuit pattern with irradiation light having a wavelength of a visible light region and a wavelength of an infrared light region, and receiving reflected light having the wavelength of the visible light region and the wavelength of the infrared light region from the electronic circuit pattern; a signal processing unit for extracting the defective pattern from a picked-up image, and determining a correcting method; a laser irradiating unit for irradiating the defective portion with laser light; and a correction determining unit for determining success or failure of defect correction before and after laser irradiation.

10 Claims, 6 Drawing Sheets

(56) References Cited

U.S. PATENT DOCUMENTS

| | | | |
|---|---|---|---|
| 2001/0020194 A1* | 9/2001 | Takagi et al. | 700/109 |
| 2006/0065645 A1* | 3/2006 | Nakasu et al. | 219/121.68 |
| 2008/0024690 A1* | 1/2008 | Hirakata et al. | 349/54 |
| 2012/0077408 A1* | 3/2012 | Tajima | 445/2 |

FOREIGN PATENT DOCUMENTS

| | | |
|---|---|---|
| JP | 2008-032433 | 2/2008 |
| JP | 2008-147321 | 6/2008 |
| WO | WO 2004/083901 | 9/2004 |

* cited by examiner

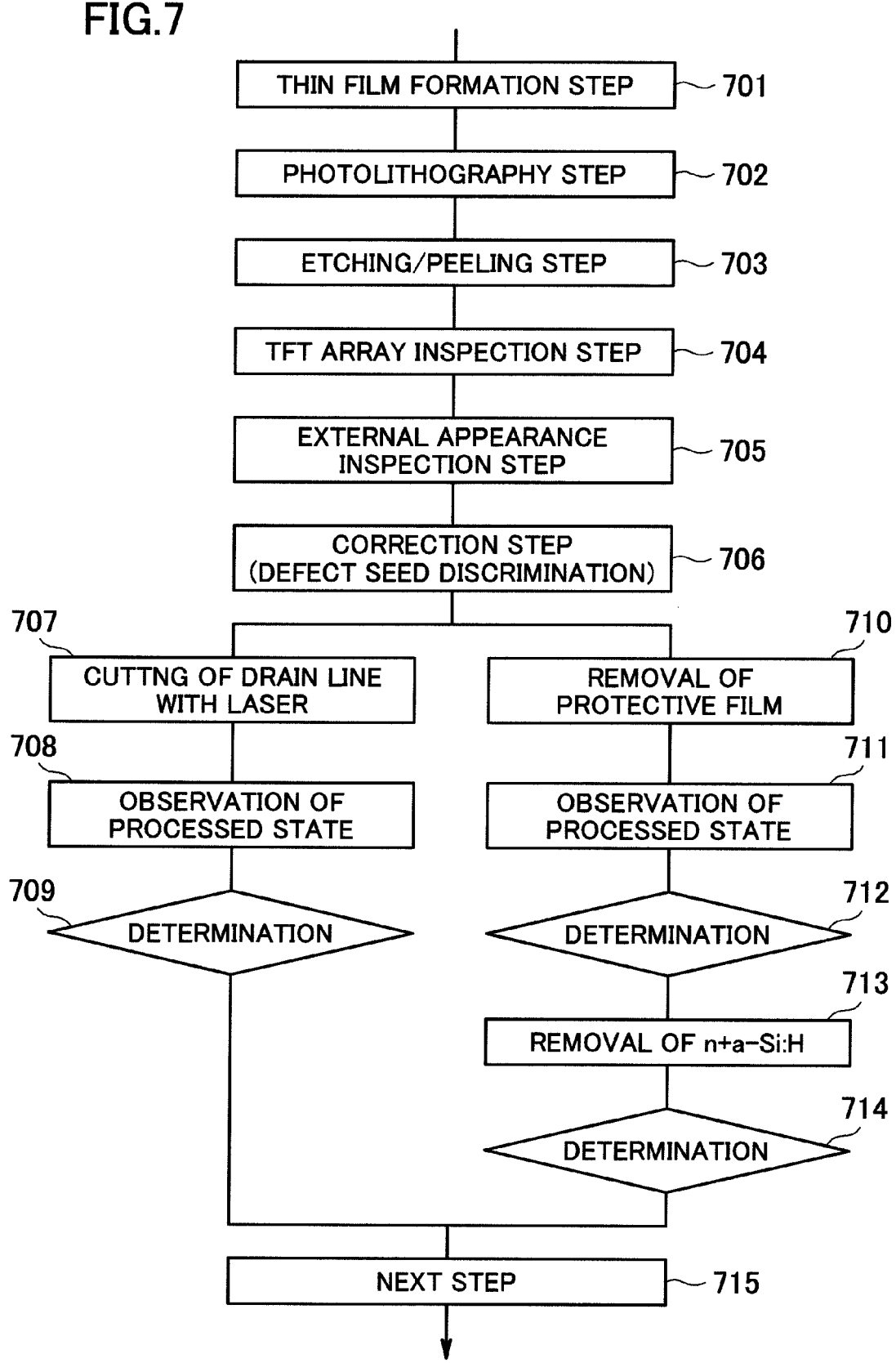

DEFECT CORRECTING METHOD AND DEFECT CORRECTING DEVICE FOR AN ELECTRONIC CIRCUIT PATTERN

CROSS-REFERENCE TO RELATED APPLICATION

The present application claims priority from Japanese application JP 2009-127619 filed on May 27, 2009, the content of which is hereby incorporated by reference into this application.

BACKGROUND OF THE INVENTION

1. Field of the Invention

The present invention relates to a defect correcting method and a defect correcting device for an electronic circuit pattern. For example, the present invention relates to a defect correcting method and a defect correcting device for an electronic circuit pattern formed on a liquid crystal display panel.

2. Description of the Related Art

A liquid crystal display panel has, for example, a configuration in which liquid crystal is interposed between a pair of glass substrates opposed to each other. Formed on a liquid crystal side surface of one glass substrate (so-called color filter substrate) is a color filter alternately coated with blue, green, and red resins. On a liquid crystal side surface of another substrate (so-called TFT substrate), a pixel circuit, wiring, a pixel driving circuit, and the like including thin film transistors (TFTs) are formed.

In this case, if pattern defects occur in the color filter or wiring, a display becomes abnormal, thereby being a defective product of the liquid crystal display panel. Examples of the display abnormality include a color defect which is caused when the resin formed on the color filter extends to an adjacent pixel and coating unevenness which is caused by the non-uniform thickness of the resin on the color filter substrate side, and disconnection of wiring or short-circuit in the wiring on the TFT substrate side.

The color filter, pixel circuit, wiring, and the like of the liquid crystal display panel are formed by laminating patterned insulating layer, conductive layer, semiconductor layer, and the like. Therefore, the pattern defect needs to be corrected after an upper layer pattern is formed or after a circuit is completed. As a method of detecting a circuit pattern defect, a general pattern inspection device using image processing or an inspection device of detecting short-circuit and disconnection electrically for an active matrix substrate may be used.

Further, as a method of correcting wiring short-circuit, a method of removing a short-circuited portion of wiring by irradiation with laser light, for example, as disclosed in JP 09-307217 A (hereinafter, referred to as Patent Document 1) is generally used. Further, for correction, an image is captured with a CCD camera, and the difference between a normal pattern and a defective pattern is detected, to thereby specify a portion to be corrected. Further, as a method of detecting a defect, a detection method of comparing the shape of an electronic circuit pattern with a normal portion is disclosed in JP 2004-279244 A (hereinafter, referred to as Patent Document 2).

SUMMARY OF THE INVENTION

According to the method disclosed in Patent Document 1, a defect is detected by an external appearance inspection device or an electric inspection device, and an operator aligns a laser irradiation region with a portion where the defect occurs and irradiates the portion with laser. Therefore, a detection element capable of visualizing such as a CCD is mounted on a device for performing correction, and the position of a defect and the seed of the defect are specified from an observed image by the detection element.

However, the detection element such as a CCD is configured so as to observe with a human's recognition wavelength (400 to 800 nm). Therefore, regarding a defect that may not be detected in the wavelength range, it is necessary to adopt an electric inspection and to correct the defect based on a defect coordinate and information detected by the inspection. Then, regarding a bright-spot defect based on short-circuit, a pixel portion provided with a thin film transistor TFT is electrically isolated, that is, a so-called black-spot forming correction is performed.

For example, in the case where a semiconductor layer is formed of amorphous silicon (a-Si) in a thin film transistor TFT, for example, an n-type amorphous silicon layer (n+a-Si layer) of a high concentration is formed at an interface between a source electrode and a drain electrode. The purpose for this is to allow the n+a-Si layer to function as a contact layer. The n+a-Si layer is formed in an upper layer of a-Si, a source electrode and a drain electrode are formed, after that, the source electrode and the drain electrode are masked, the n+a-Si layer exposed from the source electrode and the drain electrode is etched, and the remaining n+a-Si layer is configured as a contact layer.

In this case, if the n+a-Si layer exposed from the source electrode and the drain electrode is not completely etched, short-circuit may occur between the source electrode and the drain electrode, which is difficult to recognize due to the small difference in optical characteristics in a CCD observation region. Therefore, a pixel is uniformly subjected to black-spot forming for the short-circuit of the source and drain electrodes of the thin film transistor TFT.

Further, in the inspection method of Patent Document 2, only a defect that may be detected with visible light is detected, and all the defects detected by an electric inspection such as an allay tester may not be made obvious.

An object of the present invention is to provide a defect correcting method and a defect correcting device for an electronic circuit pattern, which are capable of making a defect seed of a defect detected by an electric inspection or the like obvious, which used to be difficult to recognize by observation with a conventional correcting device, and normalizing a pixel or forming a pixel into a semi-black spot.

The present invention detects, in a thin film transistor with a drain electrode and a source electrode formed on an upper surface of a semiconductor layer via a high-concentration semiconductor layer, presence/absence of a residue of the high-concentration semiconductor layer on the semiconductor layer between the drain electrode and the source electrode by imaging with irradiation light having a wavelength of an infrared light region.

The configuration of the present invention may be, for example, described as follows.

(1) According to the present invention, there is provided a defect correcting device for an electronic circuit pattern, for correcting a defect of the electronic circuit pattern formed on a substrate to normalize the electronic circuit pattern based on inspection data of an inspection device, the defect correcting device including:

an inspection data receiving unit for receiving the inspection data from the inspection device;

an imaging unit for irradiating a defective portion of the electronic circuit pattern with irradiation light having a wavelength of a visible light region and a wavelength of an infrared light region, and receiving reflected light having the wavelength of the visible light region and the wavelength of the infrared light region from the electronic circuit pattern;

a signal processing unit for extracting the defective portion of the electronic circuit pattern from a picked-up image obtained by the imaging unit, and determining a correcting method; and a laser irradiating unit for irradiating the defective portion of the electronic circuit pattern with laser light.

(2) According to the present invention, the defect correcting device for an electronic circuit pattern according to Item (1) further includes a correction determining unit for determining success or failure of defect correction of the electronic circuit pattern based on the reflected light received by the imaging unit before and after laser irradiation by the laser irradiating unit.

(3) According to the present invention, in the defect correcting device for an electronic circuit pattern according to Item (1), the laser irradiating unit processes and removes only a semiconductor layer and an insulating layer in the electronic circuit pattern in which the semiconductor layer and the insulating layer are laminated on metal wiring.

(4) According to the present invention, in the defect correcting device for an electronic circuit pattern according to Item (1), the imaging unit picks up an image using light in a range of 170 nm to 1,500 nm.

(5) According to the present invention, in the defect correcting device for an electronic circuit pattern according to Item (1), the imaging unit includes an optical element for correcting detect position information based on the wavelength of the visible light region and the wavelength of the infrared light region.

(6) According to the present invention, there is provided a defect correcting method for an electronic circuit pattern obtained by forming one of an inorganic substance and an organic substance on a substrate, followed by resist coating, light exposure, development, and etching successively, the defect correcting method including:

detecting a short-circuit defect from an imaging signal of both a wavelength of a visible light region and a wavelength of an infrared light region with respect to a material with high conductivity causing the short-circuit defect; and correcting the electronic circuit pattern by irradiating the short-circuit defect with a laser based on the detection result.

(7) According to the present invention, in the defect correcting method for an electronic circuit pattern according to Item (6), the irradiating with the laser includes laser processing performed using at least two wavelengths, that is, a laser wavelength for processing an insulating layer and a laser wavelength for processing a semiconductor layer, with respect to the electronic circuit pattern in which a semiconductor layer and an insulating layer are laminated on metal wiring.

(8) According to the present invention, there is provided a defect correcting method for an electronic circuit pattern including a thin film transistor with a drain electrode and a source electrode formed on an upper surface of a semiconductor layer via a high-concentration semiconductor layer, the defect correcting method including detecting presence/absence of a residue of the high-concentration semiconductor layer on the semiconductor layer between the drain electrode and the source electrode by imaging with irradiation light having a wavelength of an infrared light region.

The above-mentioned configuration is merely an example, and the present invention may be modified appropriately within a range not deviating the technical concept. Further, examples of the configuration of the present invention other than the above-mentioned configuration are made clear from the entire description or drawings of the present application.

According to a defect correcting method and a defect correcting device for an electronic circuit pattern described above, it is possible to make a defect seed of a defect detected by an electric inspection or the like obvious, which used to be difficult to recognize by the observation with a conventional correcting device, and to normalize a pixel or form a pixel into a semi-black spot.

The other effects of the present invention are made clear from the entire description of the specification.

BRIEF DESCRIPTION OF THE DRAWINGS

In the accompanying drawings:

FIG. 7 is a flowchart illustrating a TFT process and a correction process; and

DETAILED DESCRIPTION OF THE INVENTION

The present invention is described by way of embodiments with reference to the drawings. In each figure and each embodiment, the same or similar components are denoted with the same reference symbols, and the description thereof is omitted.

In the following, although a liquid crystal display panel is exemplified, the present invention is applicable to correction of a display panel using a general active matrix substrate. Thus, the present invention may also be applied to another display panel such as an organic electro luminescence (EL) display panel.

Embodiment 1

Figure 2:
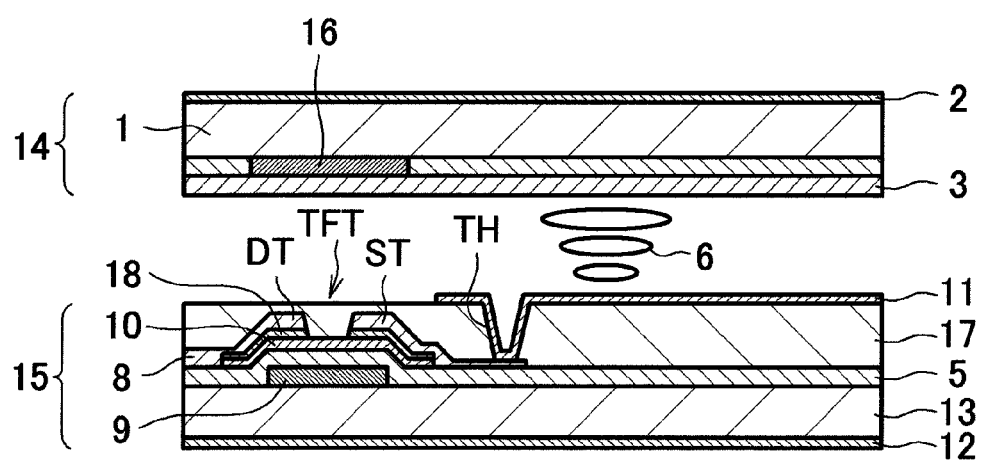
FIG. 2 is a cross-sectional view illustrating a liquid crystal display panel.

FIG. 2 is a cross-sectional view illustrating a configuration of a liquid crystal display panel to which the present invention is applied. The liquid crystal display panel has a configuration in which liquid crystal 6 is interposed between a TFT substrate 15 and a filter substrate 14 which are provided so as to be opposed to each other.

The TFT substrate 15 is configured as follows. A pixel on a surface of a glass substrate 13 on the liquid crystal 6 side includes a thin film transistor TFT that is turned on with a scanning signal to a gate electrode 9 forming a part of a gate signal line (denoted with reference symbol 9 in FIG. 2) and a pixel electrode 11 supplied with a video signal from a drain signal line (denoted with reference symbol 8 in FIG. 2) through the thin film transistor TFT that has been turned on. The thin film transistor TFT includes a semiconductor layer 10 made of, for example, amorphous silicon formed across the gate electrode 9 on an upper surface of a gate insulating film 5 formed so as to cover the gate electrode 9, and a drain electrode DT and a source electrode ST disposed via a contact layer 18 on an upper surface of the semiconductor layer 10. The contact layer 18 is formed by laminating, for example, amorphous silicon (high-concentration semiconductor layer) doped with n+ type impurities on the semiconductor layer 10, forming the drain electrode DT and the source electrode ST, etching portions exposed from the drain electrode DT and the source electrode ST, and leaving the high-concentration semiconductor layer at an interface between the drain electrode DT and the source electrode ST, in a production process of the thin film transistor TFT. The drain electrode DT is connected to a drain signal line (not shown) (denoted with reference symbol 8 in FIG. 2), and the source electrode ST is electrically connected to the pixel electrode 11. The pixel electrode 11 is formed on an upper surface of a protective film 17 formed so as to cover the thin film transistor TFT and connected to the source electrode ST through a through-hole TH formed in a protective film 17. The pixel electrode 11 is formed of a transparent conductive film made of, for example, indium tin oxide (ITO). Further, regarding the protective film 17, direct contact with the liquid crystal 6 of the thin film transistor TFT is avoided, and hence the characteristic of the thin film transistor TFT is stabilized.

The filter substrate 14 is configured as follows. On a surface of a glass substrate 1 on the liquid crystal 6 side, a black matrix (light-shielding film) 16 is formed between adjacent pixels, and a color filter is formed in the region of each pixel. Further, on upper surfaces of the black matrix (light-shielding film) 16 and the color filter, a counter electrode 3 is formed. The counter electrode 3 is formed of a transparent conductive film, for example, formed of indium tin oxide (ITO).

Although not shown, on a surface of the TFT substrate 14 on the liquid crystal 6 side and a surface of the color filter substrate 15 on the liquid crystal 6 side, alignment films for determining the initial alignment direction of the molecules of the liquid crystal 6 are formed respectively. Further, on a surface of the TFT substrate 14 on the opposite side of the liquid crystal 6 and a surface of the color filter substrate 15 on the opposite side of the liquid crystal 6, polarizing plates 2 and 12 are disposed respectively. The polarizing plates 2 and 12 are disposed so as to visualize driving of the molecules in the liquid crystal 6.

Figure 3:
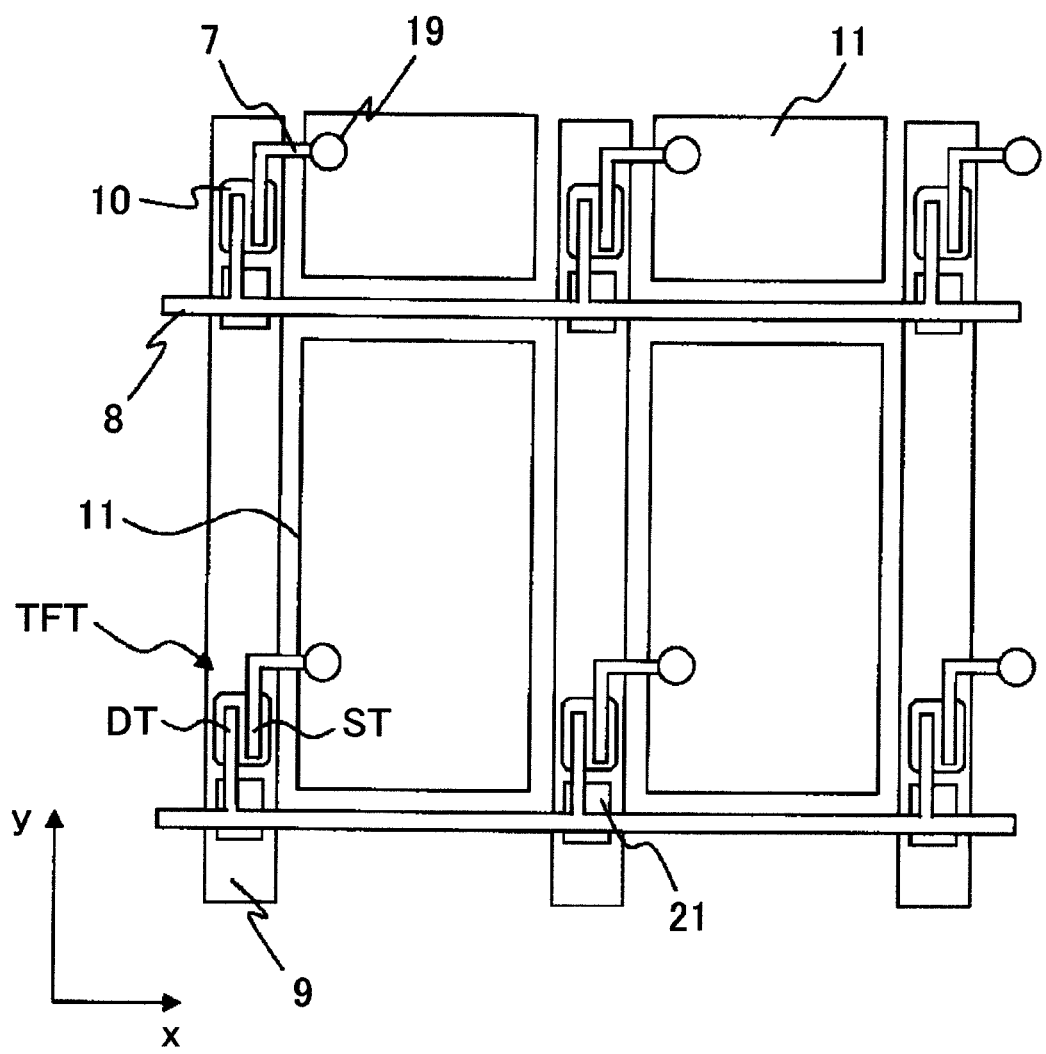
FIG. 3 is a plan view of a TFT substrate viewed from a liquid crystal side.

FIG. 3 is a plan view of the TFT substrate 15 of the liquid crystal display panel viewed from the liquid crystal 6 side. Various signal lines and electrodes formed on the TFT substrate 15 are configured as a thin film multi-layered circuit with an insulating layer interposed.

As illustrated in FIG. 3, the gate signal lines 9 extending in a y-direction and arranged in parallel in an x-direction are formed. Regions surrounded by the gate signal lines 9 and the drain signal lines 8 described later are pixel regions. The gate insulating film 5 (see FIG. 2) is formed so as to cover the gate signal lines 9, and the island-shaped semiconductor layers 10 are formed on the upper surface of the gate insulating film 5 so as to superimpose the gate signal lines 9. The semiconductor layer 10 is formed of, for example, a hydrogenated amorphous silicon a-Si:H (hydrogenated amorphous silicon) layer that is an active layer. The semiconductor layer 10 is a semiconductor layer of the thin film transistor TFT and formed for each pixel. On the upper surface of the gate insulating film 5, the drain signal lines 8 extending in the x-direction and arranged in parallel in the y-direction are formed. Each drain signal line 8 has a portion extending in each pixel, and the extending portion extends to the surface of the semiconductor layer 10 of each pixel to form the drain electrode DT of the thin film transistor TFT. Further, the source electrode ST of the thin film transistor TFT is also formed when the drain signal line DL is formed. The source electrode ST includes an extending portion extending from the surface of the semiconductor layer 10 to the pixel region side. The extending portion forms a pad 19 to be electrically connected to a pixel electrode described later. Although not shown, as described above, the contact layer 18 is formed at the interface between the drain electrode DT and the source electrode ST of the semiconductor layer 10, and the contact layer is formed of hydrogenated amorphous silicon (n+a-Si:H) doped with high-concentration n-type impurities. On the surface on which the thin film transistor TFT is formed, the protective film 17 (see FIG. 2) covering the thin film transistor TFT is formed, and on the upper surface of the protective film 17, a plane-shaped pixel electrode 11 is formed for each pixel region. The pixel electrode 11 is formed of a transparent conductive film, for example, made of indium tin oxide (ITO). The pixel electrode 11 is electrically connected to the source electrode ST of the thin film transistor TFT through the through-hole TH formed previously in the protective film.

The thin film multi-layered electronic circuit formed on the TFT substrate 15 as described above is formed by photolithography. More specifically, for example, in the case of forming signal lines, a material for the signal lines is formed uniformly over the entire region of the glass substrate 13, and the material is coated with a photoresist that is photosensitive resin. Then, the material is irradiated with UV-light through a mask corresponding to the pattern of the signal lines, to thereby expose the photoresist to light. The photoresist is developed to remove a portion exposed to light, and thus the pattern of the photoresist is formed. Further, the signal lines corresponding to the mask pattern are formed through an etching step and a resist peeling step. The same steps are performed even in the case of forming the semiconductor layer 10, and those steps are repeated for each layer, to thereby form a thin film multi-layered electronic circuit.

In the production process of the TFT substrate 15, a defect may occur in the electronic circuit pattern due to the influence by a foreign matter on a substrate or a problem in the process. When an electronic circuit pattern formed on the TFT substrate 15 of the liquid crystal display device is short-circuited or disconnected, an electric signal is not sent correctly, to thereby cause an error display. Therefore, the circuit may be corrected by cutting the short-circuited portion with a laser or the circuit may be corrected by adding a new material to a missing portion.

Figure 4:
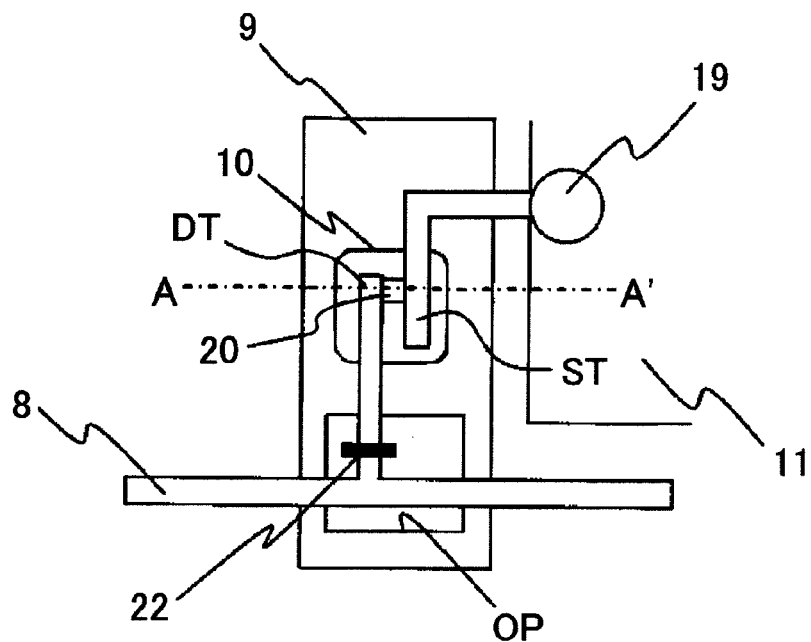
FIG. 4 is a view illustrating a short-circuit defect of a TFT substrate.

FIG. 4 is a view illustrating a portion in which the thin film transistor TFT is formed in an enlarged state in the configuration illustrated in FIG. 3, and illustrates that a short-circuit defect (denoted with reference symbol 20 in FIG. 4) occurs between the source electrode ST and the drain electrode DT of the thin film transistor TFT.

In a liquid crystal display device, in the case of a normally black system in which a black display is performed when an electric field is not applied to a pixel, when the short-circuit defect 20 occurs between the source electrode ST and the drain electrode DT, the pixel is always lit irrespective of the control of the thin film transistor TFT, which leads to a so-called bright-spot defect. The bright-spot defect is a critical defect as the display device, and the display device with such a defect is determined as a defective product. Therefore, according to a correcting method that has been used conventionally with respect to this defect, as illustrated in FIG. 4, a portion at some midpoint in a wiring path extending from the drain signal line 8 to the drain electrode DT of the thin film transistor TFT is cut with a laser (cut portion 22 is illustrated in FIG. 4), and thus a bright spot that is a critical defect is formed into a black spot. An opening OP is previously formed in the gate signal line 9 in expectation of the above-mentioned correction. Here, most of the causes of the short-circuit defect 20 are short-circuit caused by a residue of a metal material formed when the drain electrode DT and the source electrode ST are patterned or a residue formed when the contact layer 18 is etched.

Figure 5:
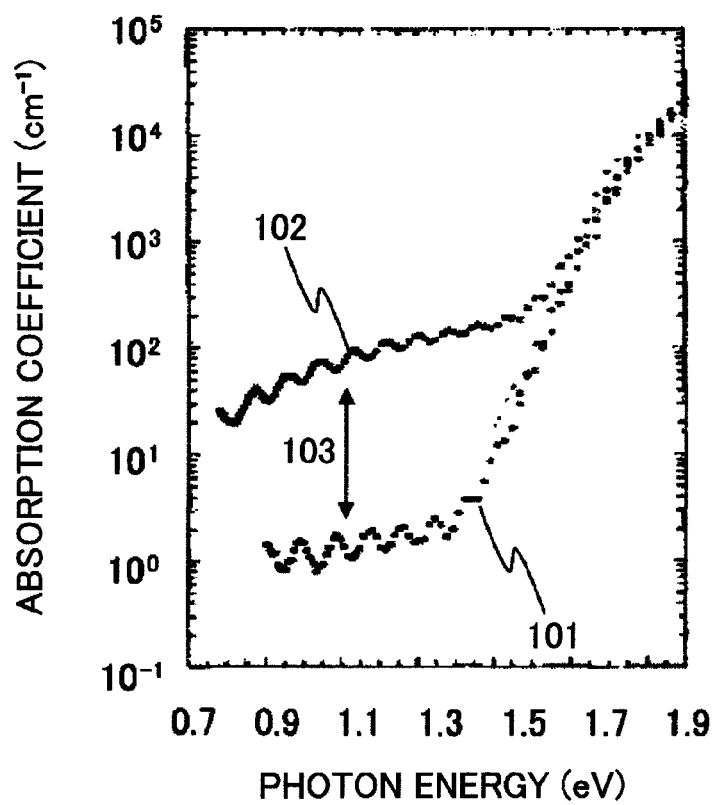
FIG. 5 is a diagram illustrating absorption characteristics of an a-Si:H thin film.

In this case, most of the metal material has a high reflectance, such as Al, and hence, a high contrast image is obtained by observing white light (visible light in 400 to 800 nm) used generally in an optical system. Therefore, an operator may check the short-circuit defect 20 by visual inspection. Further, the short-circuit defect 20 may be detected automatically, using the comparison between a normal portion and an electronic circuit pattern used often in a semiconductor inspection device or the like. However, a sufficient contrast image of a residue of the contact layer 18 may not be obtained with white light, and thus, the detection of a short-circuit defect based on the residue of the contact layer 18 is very difficult. FIG. 5 is a graph with a horizontal axis representing photon energy (eV) and a vertical axis representing an absorption coefficient (cm-1), illustrating an absorption spectrum (denoted with reference symbol 101 in FIG. 5) of an a-Si:H thin film used as the semiconductor layer 10 of the thin film transistor TFT and an absorption spectrum (denoted with reference symbol 102 in FIG. 5) of a n+a-Si:H thin film (a-Si:H thin film doped with phosphorus) used as the contact layer 18. As is apparent from FIG. 5, the absorption coefficient of any of the thin films is large in a visible light region and decreases with the decrease in energy (in a long wavelength region). The light absorption characteristics become substantially different in less than the vicinity of 1.6 eV (800 nm), and thus, the n+a-Si:H thin film shows characteristics of larger absorption compared with the a-Si:H thin film (difference therebetween is denoted with reference symbol 103 in FIG. 5).

Figure 6A:
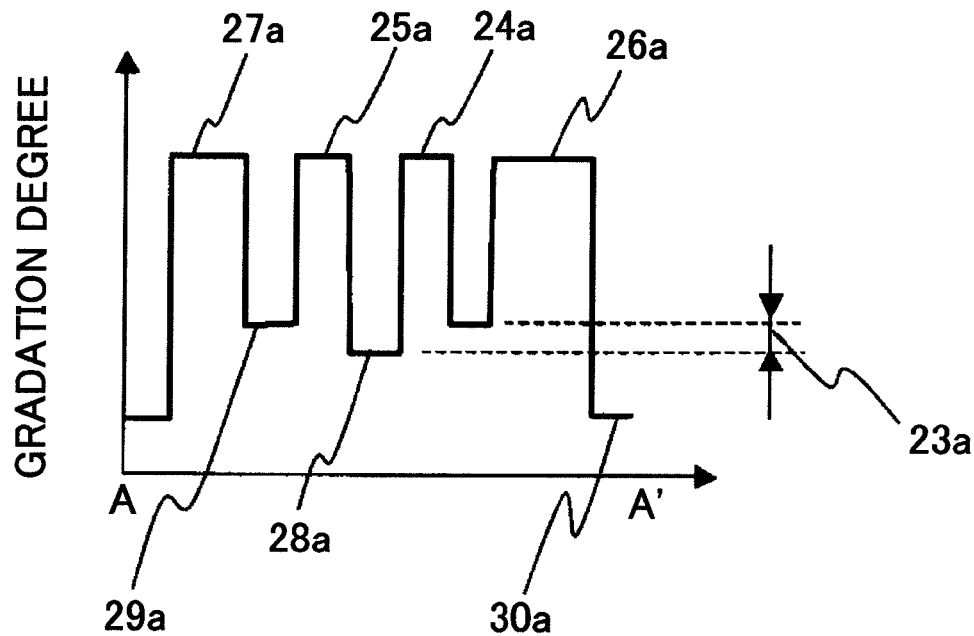
FIG. 6A is a graph illustrating an image signal in a visible light region.
Figure 6B:
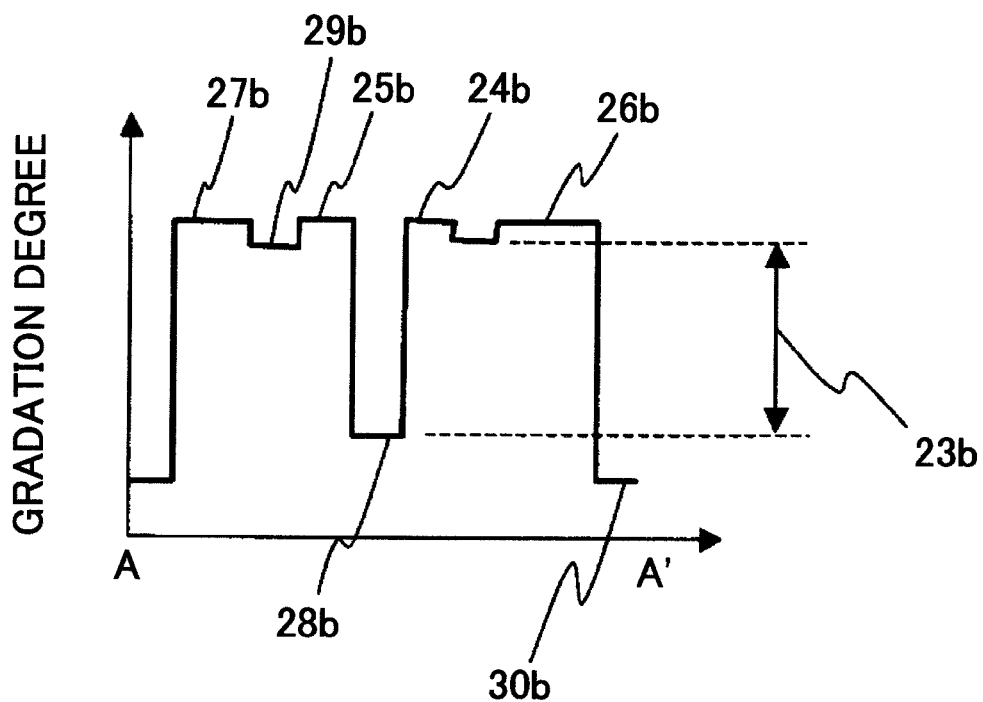
FIG. 6B is a graph illustrating an image signal in an infrared light region.

FIGS. 6A and 6B respectively illustrate an image signal (gradation degree) obtained along the line A-A' of FIG. 4. FIG. 6A illustrates an image signal (gradation degree) in the case of showing a short-circuit defect caused by a residue of a metal material, and FIG. 6B illustrates an image signal (gradation degree) in the case of showing a short-circuit defect caused by a residue of the n+a-Si:H layer. In the pixel portion (portion denoted with reference symbol 30a in FIG. 6A), the gradation degree is small because light is transmitted therethrough, and in the gate signal lines (portions denoted with reference symbols 27a and 26a in FIG. 6A), the drain signal line (portion denoted with reference symbol 25a in FIG. 6A), and the source electrode (portion denoted with reference symbol 24a in FIG. 6A), the gradation degree is large because the reflectance is large.

In the observation of the visible light region using white light, the absorption coefficient of the a-Si:H layer 10 is large, the reflected light from the gate signal lines 9 that are metal films of a lower layer is reduced, and an image signal is weak (portion denoted with reference symbol 29a in FIG. 6A). Further, the absorption characteristics in the visible light region of the short-circuit defect 20 portion caused by the residue of the n+a-Si:H layer 18 are about the same as those of the a-Si:H layer 10. Therefore, there is no large difference in reflected light between the short-circuit defect 20 portion and the a-Si:H layer 10 (portion denoted with reference symbol 28a in FIG. 6A). In FIG. 6A, the difference in gradation degree caused by the thickness fluctuation of several nm to tens of nm due to the residue of the film is observed (denoted with reference symbol 23a in FIG. 6A). Therefore, it is difficult for the operator to make a determination based on visual inspection, and a defect position may not be specified. Further, the contrast difference between the short-circuit defect 20 portion and the a-Si:H layer 10 that is not short-circuited is small, and hence the detection precision of a defect is degraded in the automatic correction by automatic recognition of the short-circuit defect 20.

On the other hand, as the absorption characteristics illustrated in FIG. 5, on the lower energy side, i.e., on the long wavelength side of 800 nm or more, the absorption characteristics of the a-Si:H layer 10 and the absorption characteristics of the n+a-Si:H layer 18 are largely different. This shows that free electrons in the n+a-Si:H layer 18 are active to infrared light, and the transmittance decreases due to the influence of scattering of the free electrons.

In contrast, in the a-Si:H layer 10, the absorption of an infrared light region is weak and characteristics of transmittance are shown, and hence, there is a difference in gradation degree in reflected light of the short-circuit defect 20 portion caused by the residue of the n+a-Si:H layer 18. Then, the long wavelength of about 800 nm to 1,500 nm is observed using observation light. As is confirmed from FIG. 6B, the pixel electrode 11 portion is transparent, and hence, reflected light is weak and the gradation degree is low (portion denoted with reference symbol 30b in FIG. 6B). In the gate signal lines 9, the drain signal lines 8, and the source electrodes 7 which are metal layers, the reflected light is strong even in an infrared light region and the gradation degree is large (portions denoted with reference symbols 24b, 25b, 26b, 27b in FIG. 6B). This is because metal material generally have strong reflection characteristics in a wide wavelength range extending from a UV region to an infrared light region. In the a-Si:H layer 10, the absorption characteristics in the infrared light region are small, and hence, the reflected light from the gate signal lines 9 which are metal films is larger compared with that in the visible light region (portion denoted with reference symbol 29b in FIG. 6B). On the other hand, in the observation image of the short-circuit defect 20 portion caused by the residue of the n+a-Si:H layer 18, the gradation degree is small (portion denoted with reference symbol 28b in FIG. 6B). This is because, the absorption in 800 nm or more occurs, and the light absorption when infrared light is reflected from the gate signal lines 9 is larger than that of the a-Si:H layer 10, as illustrated in FIG. 5. Thus, by making observation using infrared light, the contrast difference between the a-Si:H layer 10 that is a normal portion and the short-circuit defect 20 portion becomes large (denoted with reference symbol 23b in FIG. 6B), and the recognition ratio of the short-circuit defect 20 portion by the operator is enhanced, and a defect may be corrected precisely. Further, the automatic defect detection by image signal processing may also be performed based on a signal intensity difference denoted with reference symbol 23b in FIG. 6B, and the short-circuit defect 20 portion is made obvious, which enables the automation of correction.

Figure 1:
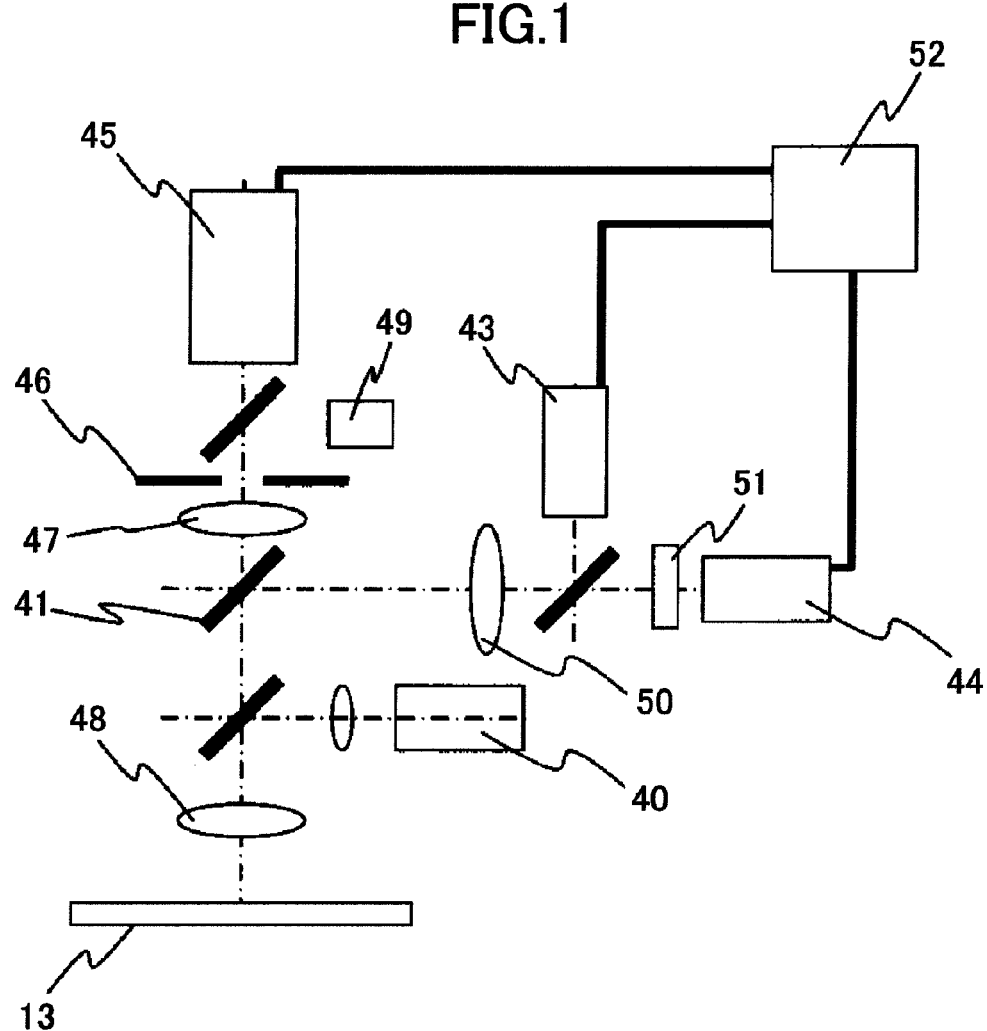
FIG. 1 is a structural view illustrating an embodiment of a defect correcting device for an electric circuit pattern according to the present invention.

FIG. 1 is a view illustrating a configuration of a correcting device (defect correcting device for an electronic circuit pattern) preferable for correcting the short-circuit defect 20 described above.

In a coaxial optical system, the correcting device includes an optical system capable of observing two wavelength regions, that is, a white light region (visible light region) which has been used at least in observation and an infrared light region for making a residue of the n+a-Si:H layer 18 obvious. Here, the wavelength region does not refer to a wavelength region in a narrow band such as several nm to tens of nm of laser light or an interference filter, but a wavelength region of at least 100 nm or more. The infrared wavelength is set at 800 to 1,500 nm from the use of a halogen lamp generally used as a light source for illumination 40 and the transmittance characteristics of quartz that is an optical system material such as a lens, so as to be used by an optical system in a visible light region.

The illumination 40 is radiated to the TFT substrate 13 after the non-uniformity of a light amount is corrected. The reflected light enters an observation optical system via an objective lens 48, a half mirror 41, and an image-forming lens 50. Here, the reflected light is divided into infrared light and visible light by a dichroic mirror 42, and light signals are sent to an imaging element 43 for infrared light and an imaging element 44 for visible light, such as a CCD, which have sensitivity with respect to the respective wavelengths. A far-infrared cut-filter 51 is set in front of the imaging element 44 for visible light, and the noise of a visible light image is reduced. As the objective lens 48 and the image-forming lens 50 of the observation optical system, a lens with color aberration corrected in a visible light region and an infrared light region is used. Further, by disposing the image-forming lens at the back of the dichroic mirror 42 and disposing a diffraction optical element having a function of color aberration correction in the observation optical system, the defect position precision and the displacement of a focus position by a wavelength may be removed.

The detection of a defect by the correcting device is performed using observation image signals of both infrared light and visible light. The inspection of an external appearance conducted in the production step of the TFT substrate 13 is performed in the visible light region, and the review in the correcting device by visible light is necessary for reproducing the detected defect. Further, infrared light for making a defect caused by a residue of the n+a-Si:H layer 18 obvious is used in addition to the observation in the visible light region, with respect to the defect detected by an electric inspection. The imaging element of infrared light is likely to generate noise due to a change in temperature, and hence, the temperature of the element may be managed so as to perform stable detection.

A pulse laser 45 for processing is mounted coaxially with the observation optical system. The pulse laser 45 oscillates a yttrium aluminum garnet (YAG) fundamental harmonic (1,064 nm) or a second harmonic (532 nm) for processing a metal film, and a UV laser (266 nm) as a fourth harmonic for processing a SiN thin film that is a protective film. The light from the pulse laser 45 passes through a slit 46 which is changeable and set in the optical system, and projected with the size reduced onto the TFT substrate 13 via an image-forming lens 47 and the objective lens 48. Guide light 49 for adjusting the slit position is set in the slit 46, to thereby determine the irradiation position of the pulse laser 45.

As described above, by setting the observation optical system in the infrared light region together with the observation optical system in the white light (visible light) region in the correcting device, the short-circuit defect 20 (FIG. 4) caused by the residue of the n+a-Si:H layer 18 which has been difficult to detect conventionally may be detected, cutting is performed with the pulse laser 45, and a bright-spot defect may be corrected by black-spot forming. This enables the enhancement of the relief ratio of a defect.

Embodiment 2

Next, as Embodiment 3 of the present invention, a description is made regarding a correcting method by performing normalization or formation of a semi-black spot with respect to short-circuit of the source electrode ST and the drain electrode DT caused by a residue of the n+a-Si:H layer 18 in the thin film transistor TFT.

In Embodiment 2, a bright-spot defect is not formed into a black spot, and only the short-circuit defect 20 portion is processed with the pulse laser 45, and thus the short-circuit defect 20 is corrected so as to be normalized or formed into a semi-black spot. Here, the semi-black-spot forming refers to a state in which a black display is performed at all times when the thin film transistor TFT is turned off, and the thin film transistor TFT may be lit although the brightness is lower compared with that of a normal pixel when the thin film transistor TFT is in an ON state.

The short-circuit defect 20 occurs in the case where metal wiring or n+ wiring remains in a part of the source electrode ST and the drain electrode DT. Conventionally, even in the case where a part of the source and drain electrodes is short-circuited, the correction is performed by black-spot forming of cutting an extended portion of the drain electrode 8, as described in FIG. 4. However, in many cases the short-circuit defect 20 is caused by short-circuit at only a part (10% or less) of the electrodes, and the short-circuit may be corrected by removing only this part.

FIG. 7 illustrates the inspection correction process of the short-circuit defect 20. In the same way as in Embodiment 1, the production process of the thin film transistor TFT includes a thin film formation step 701 of forming wiring and a semiconductor active layer, a photolithography step 702 of forming an electronic circuit pattern, and an etching/peeling step 703. A TFT array is completed by repeating those steps, and the presence/absence of a defect may be checked in the TFT array inspection step 704 and the external appearance inspection step 705 that are electric inspection. The inspection step may be performed in each layer of the TFT wiring, or only the electric inspection or the external appearance inspection may be used.

The TFT substrate 13 in which a defect is detected in the inspection step is transported to a correction step 706 together with defect seed information and defect position information. In the correction step 706, the vicinity of the short-circuit defect 20 portion of the TFT substrate 13 is picked up, using the wavelength in the visible light region and the wavelength in the infrared light region, described in Embodiment 1. The portion corresponding to the defect position coordinate sent from the inspection device is observed and the short-circuit defect 20 is made obvious, and thus a defect position and a defect seed may be determined with further higher precision. When the short-circuit defect 20 is made obvious, the picked-up image of the visible light region is used for detecting the short-circuit defect 20 caused by the residue of the metal thin film, and the picked-up image in the infrared light region is used for detecting the short-circuit defect 20 caused by the residue of the n+a-Si:H layer 18. Also, two images may be compared with each other depending upon the defect seed. Thus, the short-circuit defect 20 may be made further obvious.

Thus, by conducting inspection using the images corresponding to the above mentioned wavelength regions, it may be determined whether the short-circuit defect 20 of the source electrode 7 and the drain electrode 8 is caused by the residue of the metal thin film or the n+a-Si:H thin film 18. The black-spot forming correction, which is a conventional correcting method, is applied to a defect caused by a residue of the metal thin film, and an extended line of the drain signal line 8 is cut with the pulse laser 45. Regarding the processed state, the determination of the correction completion is performed by checking the remaining processing while observing with an imaging element at all times.

Figure 8A:
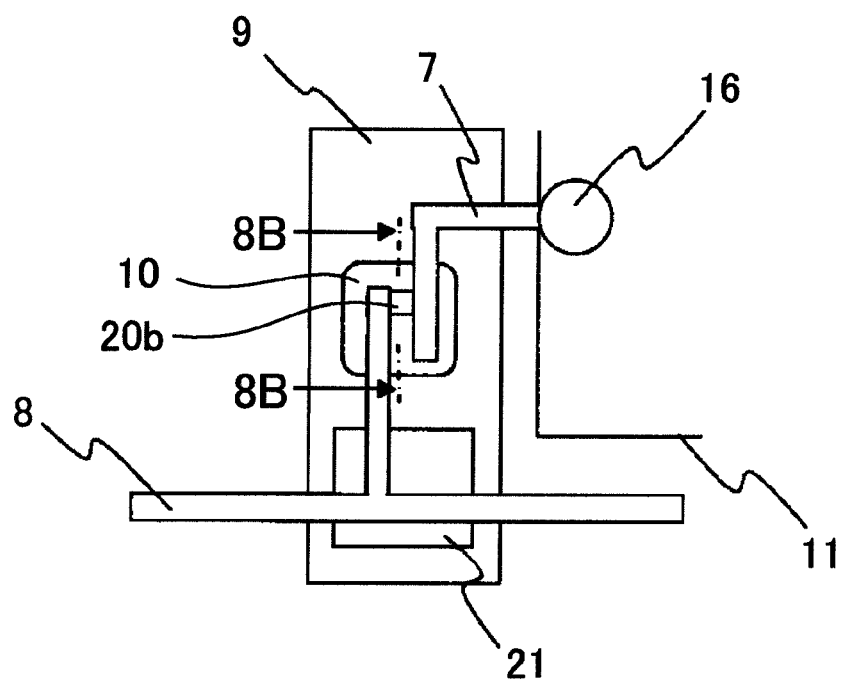
FIGS. 8A and 8B illustrate a method of correcting a short-circuit defect of the present invention.
Figure 8B:
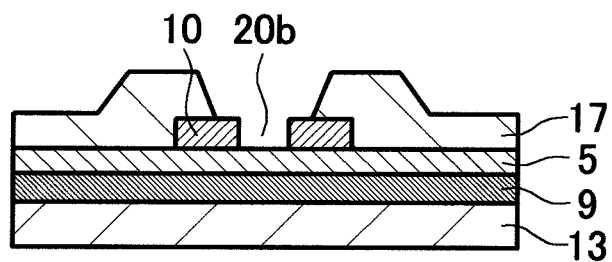

FIGS. 8A and 8B are views illustrating the short-circuit defect 20 caused by the residue of the n+a-Si:H thin film 18 is removed by the above-mentioned correcting method. FIG. 8B is a cross-sectional view taken along the line b-b of FIG. 8A. In FIGS. 8A and 8B, a hole formed in the n+a-Si:H thin film 18 and the n+a-Si:H layer 10 with a laser is denoted with reference symbol 20b in FIGS. 8A and 8B. When the short-circuit defect 20 is determined to be caused by the residue of the n+a-Si:H thin film 18 by the observation of the infrared light region, first, a window is opened by removing the protective film 17 formed in the upper layer of the short-circuit defect 20 portion. The protective film 17 is removed by a photolysis function using a UV laser. If the fourth harmonic (266 nm) of the YAG laser is used, high processing shape precision is obtained with respect to an irradiated region. The a-Si:H layer 10 of the short-circuit defect 20 portion in the lower layer appears due to the window opening. After that, a laser of visible light is radiated, with respect to which the n+a-Si:H layer 18 and the a-Si:H layer 10 show large absorption coefficients. Here, it is preferred to use the second harmonic (532 nm) of the YAG laser. The transparency of the gate insulating film 5 in the lower layer is high with respect to 532 nm, and the reflectance of the gate signal line 9 in the lower layer is high, and hence the damage with respect to laser light is small. More specifically, due to the large processing selection ratio with respect to the a-Si:H layer, only the n+a-Si:H layer 18 and the a-Si:H layer 10 of the short-circuit defect 20 may be removed.

As described above, an image signal of a detect seed is acquired by the imaging element using the wavelength of visible light and the wavelength of infrared light, and the detect seed is classified by a control device 52 performing signal processing. For classification of the defect seed, an image of infrared light, an image of visible light, or both images are used, and a desired defect is extracted. After that, a more preferred correcting method is selected by the control device 52, and the TFT substrate 13 is corrected with a wavelength suitable for the correcting method from the pulse laser 43. Therefore, the short-circuit defect 20 caused by the residue of the n+a-Si:H thin film 18, which have been difficult to detect conventionally, may be corrected, and hence the TFT substrate 13 may be formed into a satisfactory product.

In the above-mentioned embodiment, the cutting of the short-circuit defect 20 has been described. However, a device for connecting a signal line and a device for forming a thin film such as an insulating film may be mounted on the correcting device illustrated in FIG. 1 in addition to a laser processing device (cutting processing device), to thereby correct a defect efficiently.

Further, a liquid crystal display device has been exemplified in the above-mentioned embodiments. However, the present invention is not limited thereto, and the present invention may be applied to an organic electro luminescence (EL) device or a plasma display panel (PDP) device.

The present invention has been described above by way of the embodiments. However, the configurations described in the respective embodiments described above are merely examples, and modifications may be made to the present invention as appropriate without departing from the technical concept of the present invention. Besides, the configurations described in the respective embodiments may be used in combination unless a contradiction arises therebetween.

What is claimed is:

1. A defect correcting device for an electronic circuit pattern, for correcting a defect of the electronic circuit pattern including a thin film transistor with a drain electrode and a source electrode formed on an upper surface of a semiconductor layer via a high-concentration semiconductor layer formed on a substrate to normalize the electronic circuit pattern based on inspection data of an inspection device, the defect correcting device comprising:
an inspection data receiving unit for receiving the inspection data from the inspection device;
an imaging unit for irradiating a defective portion of the electronic circuit pattern with irradiation light having a wavelength of an infrared light region, and receiving reflected light having the wavelength of the infrared light region from the electronic circuit pattern;
a signal processing unit for extracting the defective portion of the electronic circuit pattern from a picked-up image obtained by the imaging unit, and detecting the defect of the electronic circuit pattern by checking presence or absence of a residue of the high-concentration semiconductor layer on the semiconductor layer between the drain electrode and the source electrode and determining a correcting method; and
a laser irradiating unit for irradiating the defective portion of the electronic circuit pattern with laser light.

2. The defect correcting device for an electronic circuit pattern according to claim 1, further comprising a correction determining unit for determining success or failure of defect correction of the electronic circuit pattern based on the reflected light received by the imaging unit before and after laser irradiation by the laser irradiating unit.

3. The defect correcting device for an electronic circuit pattern according to claim 1, wherein the laser irradiating unit processes and removes only a semiconductor layer and an insulating layer in the electronic circuit pattern in which the semiconductor layer and the insulating layer are laminated on metal wiring.

4. The defect correcting device for an electronic circuit pattern according to claim 1, wherein the imaging unit picks up an image using light in a range of 800 nm to 1,500 nm.

5. The defect correcting device for an electronic circuit pattern according to claim 1, wherein the imaging unit includes an optical element for correcting detect position information based on the wavelength of the infrared light region.

6. A defect correcting method for an electronic circuit pattern including a thin film transistor with a drain electrode and a source electrode formed on an upper surface of a semiconductor layer via a high-concentration semiconductor layer obtained by forming one of an inorganic substance and an organic substance on a substrate, followed by resist coating, light exposure, development, and etching successively, the defect correcting method comprising:
detecting a short-circuit defect by checking presence or absence of a residue of the high-concentration semiconductor layer on the semiconductor layer between the drain electrode and the source electrode from an imaging signal of a wavelength of an infrared light region;
determining a correcting method and correcting the electronic circuit pattern by irradiating the short-circuit defect with a laser in the selected correcting method.

7. The defect correcting method for an electronic circuit pattern according to claim 6, wherein the irradiating with the laser includes laser processing performed using at least two wavelengths, that is, a laser wavelength for processing an insulating layer and a laser wavelength for processing a semiconductor layer, with respect to the electronic circuit pattern in which a semiconductor layer and an insulating layer are laminated on metal wiring.

8. A defect correcting device for an electronic circuit pattern, for correcting a defect of the electronic circuit pattern formed on a substrate to normalize the electronic circuit pattern based on inspection data of an inspection device, the defect correcting device comprising:
- an inspection data receiving unit for receiving the inspection data from the inspection device;
- an imaging unit for irradiating a defective portion of the electronic circuit pattern with irradiation light having a wavelength of a visible light region and a wavelength of an infrared light region, and receiving reflected light having the wavelength of the visible light region and the wavelength of the infrared light region from the electronic circuit pattern;
- a signal processing unit for comparing two picked-up images obtained by the wavelength of a visible light and an infrared light, respectively, of the imaging unit and extracting the defective portion of the electronic circuit pattern, and determining a correcting method; and
- a laser irradiating unit for irradiating the defective portion of the electronic circuit pattern with laser light.

9. The defect correcting method for an electronic circuit pattern according to claim 8, wherein the signal processing unit more particularly utilizes the comparing of the two picked-up images to differentiate between defects caused by a residue of a metal film in comparison to defects caused by a residue of an n+a-Si layer, and more particularly, determines the correcting method for a subject defect according to whether the subject defect was determined as being caused by a residue of a metal film, or caused by a residue of an n+a-Si layer.

10. The defect correcting method for an electronic circuit pattern according to claim 9, wherein a picked-up image obtained by the wavelength of an infrared light, of the two picked-up images, is used to determine the defects caused by the residue of an n+a-Si layer.

* * * * *